United States Patent [19]

Mizushima et al.

[11] Patent Number: 5,124,352
[45] Date of Patent: Jun. 23, 1992

[54] FAT EMULSIONS CONTAINING ISOCARBACYCLIN

[75] Inventors: Yutaka Mizushima, 25-20, Daia 4-chome, Setagaya-ku, Tokyo, 155; Yoko Shoji; Yasuko Yagyu, both of Kanagawa; Seizi Kurozumi, Tokyo, all of Japan

[73] Assignees: Teijin Limited, Osaka; Yutaka Mizushima, Tokyo, both of Japan

[21] Appl. No.: 727,376

[22] Filed: Jul. 5, 1991

Related U.S. Application Data

[63] Continuation of Ser. No. 428,020, Oct. 26, 1989, abandoned, which is a continuation of Ser. No. 15,451, filed as PCT/JP86/00293, Jun. 12, 1986, abandoned.

[30] Foreign Application Priority Data

Jun. 17, 1985 [JP] Japan ................... 60-129920

[51] Int. Cl.$^5$ ............................. A61K 31/235
[52] U.S. Cl. ..................... 514/510; 514/469; 514/573
[58] Field of Search .............. 514/469, 510, 573

[56] References Cited

U.S. PATENT DOCUMENTS

| | | |
|---|---|---|
| 4,472,428 | 9/1984 | Toru et al. ............... 549/214 |
| 4,613,614 | 9/1986 | Fukaya et al. ............ 514/469 |
| 4,683,633 | 8/1987 | Imagawa et al. .......... 514/573 |

FOREIGN PATENT DOCUMENTS

| | | |
|---|---|---|
| 0097481 | 1/1984 | European Pat. Off. . |
| 0132027 | 1/1985 | European Pat. Off. . |
| 53-50141 | 5/1978 | Japan . |
| 59-210044 | 11/1984 | Japan . |
| 210044 | 11/1984 | Japan . |
| 60-13779 | 1/1985 | Japan . |
| 60-149524 | 8/1985 | Japan . |
| 60-169430 | 9/1985 | Japan . |
| 60-243079 | 12/1985 | Japan . |
| 60-260524 | 12/1985 | Japan . |
| 61-44819 | 3/1986 | Japan . |
| 2012168 | 8/1979 | United Kingdom . |

OTHER PUBLICATIONS

*Hackh's Chemical Dictionary*, McGraw-Hill 1972, p. 424.

Primary Examiner—Mary C. Lee
Assistant Examiner—Jacqueline Haley
Attorney, Agent, or Firm—Sughrue, Mion, Zinn, Macpeak & Seas

[57] ABSTRACT

The fat emulsions containing the prostaglandin $I_2$'s expressed by the following formula (I):

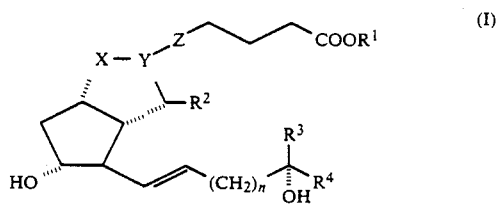

where X represents an oxygen atom to a methine group, Y is a carbon atom, Z represents a methylene or methine group; when X is an oxygen atom, the mode of Y-Z binding is a double bond of carbon-carbon, and when X is a methine group, the mode of X-Y binding is a double bond of carbon-carbon and Z is a methylene group; $R_1$ represents a hydrogen atom or alkyl group, $R_2$ represents a hydrogen atom or fluorine atom, and $R_3$ represents a hydrogen atom, methyl group, ethyl group or vinyl group. $R_4$ represents a substituted or unsubstituted alkyl group with 1–10 carbon atoms, a substituted or unsubstituted alkenyl group with 2–10 carbons atoms, a substituted or unsubstituted alkynyl group with 2–10 carbon atoms, or a substituted or unsubstituted cycloalkyl group with 3–8 carbon atoms; and n is zero (0) or an integer of value 1.

3 Claims, No Drawings

FAT EMULSIONS CONTAINING ISOCARBACYCLIN

This is a continuation of application Ser. No. 07/428,020, filed Oct. 26, 1989 abandoned which is a continuation of application Ser. No. 07/015,451 filed as PCT/JP86/00293, Jun. 12, 1986, now abandoned.

TECHNICAL FIELD

This invention relates to fat emulsions containing the prostaglandin $I_2$'s.

More particularly, it relates to new fat emulsions containing, as an active ingredient, the prostaglandin $I_2$'s which are not only thrombolytic but are useful in the treatment of cardiovascular-renal system disorders as well.

BACKGROUND OF THE INVENTION

The prostaglandins exibit a wide range of physiological activities and have been finding widespread medicinal applications because of their diverse and useful biological actions such as peripheral circulatory improvement, vasodilation, antiulceration, hypotensive, induction of labor, thrombolytic, and antiasthmatic. In recent years, these compounds have been studied for possible new indications such as anticancer, osteometabolism improvement, antiviral, hepatic protection, diuresis In particular, the naturally occurring prostacyclin is a local hormone predominantly produced in vivo from the vascular wall of arteries; owing to its potent physiological effects such as platelet agglutination inhibitory activity and vasodilating activity, this local hormone is an important factor which regulates in vivo cellular functions, and hence an attempt has been made to use the naturally occurring prostacyclin per se as a pharmaceutical product [P. J. Lewis, J. 0. Grady et al., Clinical prostacyclin, Raven Press, N.Y. (1981)].

On the other hand, however, when these useful prostaglandins are applied as pharmaceutical products, various problems are encountered with respect to the in vivo instability inherent in the prostaglandins, side effects attributable to a wide range of their physiological effects, and the difficulties of formulations due to their chemical instability.

Thus, intensive studies have been carried out at home and abroad with regard to chemically stable synthetic prostacyclin derivatives comparable to naturally occurring prostacyclin in terms of biological actions.

Meanwhile, attempts have been made to stabilize chemically unstable prostacyclin in dosage form as well as to improve its drug efficacy. For example, propositions have been put forth regarding a method of stabilizing the prostacyclin as the clathrate compound using cyclodextrin (Joseph Scesitri et al., Japan Laid-Open Patent Showa 54-56685), a method of stabilizing the prostacyclin with surface active agents (Moo Yang Chou et al., Japan Laid-Open Patent Showa 55-15470), a pharmaceutical preparation by first obtaining a new ester derivative of prostacyclin with the higher fat solubility, emulsifying this ester derivative in a fat, and maintaining its activity comparable to that of the parent prostacyclin (Fukaya et al., Japan Laid-Open Patent Showa 60-13779), and so forth.

The fat emulsions containing $PGE_1$ or $PGA_1$ have recently been proposed as the stabilized prostaglandin fat preparations which possess vasodilating, platelet agglutination inhibitory, and hypotensive activities [Mizushima et al., Japan Laid-Open Patent Showa 58-222014 and Japan Laid-Open Patent Showa 59-141518; and Mizushima et al., Ann. Rheum. Diseases, 41, 263 (1982); Pharm. Pharmacol., 35, 398 (1983)]. Such techniques are applied to the preparation of the anti-tumor agents; a proposal has been set forth with respect to the improvement of selective delivery of anticancer drugs to the target organ (Okamoto et al., Japan Laid-Open Patent Showa 59-122423).

DISCLOSURE OF THE INVENTION

The inventors noticed the aforementioned facts and made intensive studies on some of the chemically stable synthetic prostaglandin $I_2$'s in order to prolong their effects and enhance their clinical efficacy. As a consequence, we prepared said fat emulsion containing the stable prostaglandin $I_2$'s, and discovered that the said preparations have attained these objects. The inventors, therefore, arrived at the present invention This invention, therefore, concerns the fat emulsions containing the prostaglandin $I_2$'s expressed by the following formula (I):

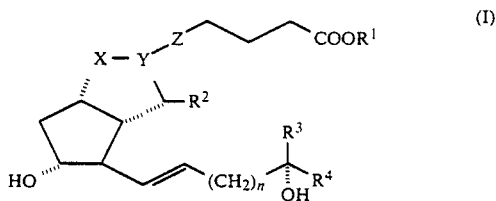

where X represents an oxygen atom or a methine group, Y is a carbon atom, Z represents a methylene or methine group; when X is an oxygen atom, the mode of Y-Z binding is a double bond of carbon-carbon; and when X is a methine group, the mode of X-Y binding is a double bond of carbon-carbon and Z is a methylene group; $R_1$ represents a hydrogen atom or alkyl group, $R_2$ represents a hydrogen atom or fluorine atom, and $R_3$ represents a hydrogen atom, methyl group, ethyl group or vinyl group. $R_4$ represents a substituted or unsubstituted alkyl group with 1-10 carbon atoms, a substituted or unsubstituted alkenyl group with 2-10 carbons atoms, a substituted or unsubstituted alkynyl group with 2-10 carbon atoms, or a substituted or unsubstituted cycloalkyl group with 3-8 carbon atoms; and n is zero (0) or an integer of value 1.

The fat emulsions in the invention are new fat emulsions containing chemically stable prostaglandin $I_2$'s; such fat emulsions possess longer duration of action, improve the stability of the prostaglandin $I_2$'s, reduce manifestation of side effects, exhibit, at the same time, potent pharmacological effects, and are useful as the preparations for use in intravenous administration.

Most of the prostaglandin $I_2$'s in the aforementioned formula (I) are the compounds known to be stabilized prostaglandin $I_2$'s [Japan Laid-Open Patent Showa 58-150583, Japanese Patent Application Number Showa 57-32981).]

In the aforementioned formula (I), X represents an oxygen atom or a methine group, Y is a carbon atom, Z represents a methylene or methine group; when X is an oxygen atom, the mode of Y-Z binding is a double bond of carbon-carbon, and when X is a methine group, the mode of X-Y binding is a double bond of carbon-carbon and Z is a methylene group. From these definitions, it is preferable in the present invention that the active ingredient is the isocarbacyclins expressed by the forllowing formula (Ia):

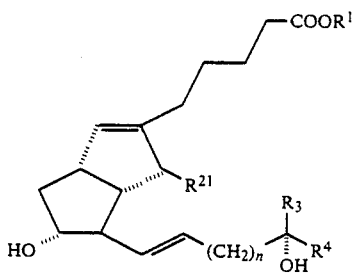

(where $R_1$, $R_3$, $R_4$, and n are defined as above; $R_{21}$ represents a hydrogen atom); or that the active ingredient is the 7-fluoroprostacyclins expressed by the following formula (Ib):

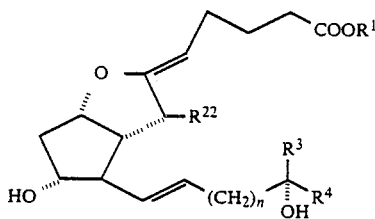

(where $R_1$, $R_3$, $R_4$, and n are defined as above; $R_{22}$ represents a fluorine atom).

In the aforementioned formula (1), $R_1$ is a hydrogen atom or alkyl group. The said alkyl group may be an alkyl group with 1-10 carbon atoms such as methyl, ethyl, propyl, butyl, pentyl, hexyl, octyl, and decyl group. The $R_1$ is preferably a hydrogen atom or methyl group.

$R_4$ represents a substituted or unsubstituted alkyl group with 1-10 carbon atoms, a substituted or unsubstituted alkenyl group with 2-10 carbon atoms, a substituted or unsubstituted alkynyl group with 2-10 carbon atoms, or a substituted or unsubstituted cycloalkyl group with 3-10 carbon atoms. The unsubstituted alkyl group with 1-10 carbon atoms may, for example, be a methyl, propyl, butyl, pentyl, hexyl, octyl, decyl group, etc. The unsubstituted alkenyl group with 2 - 10 carbon atoms may, for example, be a vinyl, 2-propenyl, 3-butenyl, 2-pentenyl, 2-methyl-3-pentenyl, 2-hexenyl, 5-methyl-4-hexenyl, 2,6-dimethyl-5-heptenyl group, etc. The unsubstituted alkynyl group with 2 - 10 carbon atoms may, for example, be a 2-butynyl, 3-butynyl, 1-methyl-2-pentynyl, 1-methyl-3-pentynyl, 2-hexynyl, 4-hexynyl group, etc. The unsubstituted cycloalkyl group with 3-8 carbon atoms may, for example, be a cyclopropyl, cyclopentyl, cyclohexyl group, etc.

Suitable substituent groups for these alkyl, alkenyl, alkynyl, and cycloalkyl groups include halogen atoms such as fluorine and chlorine; such lower alkoxy groups, such as methoxy, ethoxy, propoxy, and butoxy group; a halogenoalkyl group such as trifluoromethyl; a substituted or unsubstituted phenoxy group which has been substituted or unsubstituted with a halogen atom or a lower alkoxy group.

The prostaglandin $I_2$'s in formula (1) may be prepared, for example, according to the methods described in Japan Laid-Open Patent Showa 58-150583 and Japan Laid-Open Patent Showa 57-32981.

The stable prostaglandin $I_2$'s shown in the aforementioned formula (1) are specifically listed as follows:
(1) Isocarbacyclin, i.e. 9(O)-methano-$\Delta^{6(9\alpha)}$-$PGI_1$, (hereinafter "isocarbacyclin").
(2) 16,17,18,19,20-Pentanor-15-cyclopentylisocarbacyclin
(3) 16,17,18,19,20-Pentanor-15-cyclohexylisocarbacyclin
(4) 17,20-Dimethylisocarbacyclin
(5) 15-Deoxy-16-hydroxyisocarbacyclin
(6) 15-Deoxy-16-hydroxy-16,20-dimethylisocarbacyclin
(7) 7-Fluoroprostacyclin
(8) 7-Fluoro-16,17,18,19,20-pentanor-15cyclopentyl-prostacyclin
(9) 7-Fluoro-16,17,18,19,20-pentanor-15cyclohexyl-prostacyclin
(10) 7-Fluoro-17,20-dimethylprostacyclin
(11) 7-Fluoro-16,16-dimethylprostacyclin
(12) 7,16-Difluoroprostacyclin
(13) 15-Deoxy-16-hydroxy-7-fluoroprostacyclin
(14) 15-Deoxy-16-hydroxy-7,16-difluoroprostacyclin
(15) The methyl esters of (1) - (14)

The fat emulsions in the invention comprises, as main constituents, the prostaglandin $I_2$'s in formula (I), 5-50 w/v % of vegetable oil, 1-50 parts, preferably 5-30 parts, of phospholipid for 100 parts of the vegitable oil, and an appropriate quantity of water.

The vegetable oil may be soybean oil, cotton seed oil, sesami oil, safflor oil, and corn oil, but preferably soybean oil.

The soybean oil of choice is a refined soybean oil with high purity. Preferably, it is the highly purified, refined soybean oil obtained by further purifying common refined soybean oil by, for example, steam distillation.

The phospholipid is a purified phospholipid such as egg yolk lecithin and soybean lecithin. The phospholipid may be used which has been prepared by fractionation using an organic solvent according to a conventional method, that is, by slowly adding, with stirring, acetone to a crude yolk phospholipid dissolved in a cold n-hexane-acetone mixture, collecting insolubles by filtration, repeating the procedure of dissolution, followed by precipitation, and finally removing the solvent by distillation. The product comprises, as main constituents, phosphatidylcholine and phosphatidylethanolamine. The other phospholipids may be phosphatidylinositol, phosphatidylserine, sphingomyelin, etc.

To the fat emulsions in the invention may, where necessary, be further added an emulsifying adjuvant, stabilizer, high molecular substance, isotonizing agent, etc.

The emulsifying adjuvant may, for example, be up to 0.3 w/v % of fatty acids with 6-22, preferably 12-20, carbon atoms or their pharmaceutically acceptable salts, and so on. Either of the fatty acids with 6-22 carbon atoms may be used if they can be added to pharmaceutical products. Such fatty acids are either of the straight or of the branched chain; they are preferably stearic, oleic, linolic, palmitic, linolenic, and myristic acids. These salts may be salts with alkali metals such as sodium and potassium, with alkaline earth metals such as calcium, and so on.

The stabilizing agent may, for example, be less than 0.5 w/v %, preferably less than 0.1 w/v %, of the cholesterols, less than 5 w/v %, preferably less than 1 w/v %, of phosphatidic acids, and so forth.

The high molecular substances may, for example, be 0.1–5 parts by weight, preferably 0.5–1 part by weight, of albumin, dextran, vinyl polymers, nonionic surface active agents, gelatin, hydroxyethyl starch, etc. for 1 part by weight of the prostaglandin $I_2$'s.

The albumin may preferably be of human origin, and the vinyl polymers may be polyvinylpyrrolidone, etc. The nonionic surface active agents may, for example, be polyalkylene glycols, polyoxyalkylene copolymers, the polyoxyalkylene derivatives of hardened castor oil, the polyoxyalkylene derivatives of castor oil, etc.

The content of the prostaglandin $I_2$'s in the fat emulsions may be suitably increased or decreased according to the form of the emulsions and applications; in general, minute quantities, for example, 1.0 mg–0.2 µg/ml in the fat emulsions are sufficient.

The fat emulsions in the present invention are prepared, for example, in the following manner: Predetermined amounts of vegetable oil, phospholipid, the prostaglandin $I_2$'s, and other additives are mixed and the mixture is warmed to a solution. The solution is homogenized by, for example, the use of a homogenizer of the high-pressure jet type, an ultrasonic homogenizer, etc. The homogenate is further homogenized following the addition of a necessary amount of water in order to prepare the fat emulsions in the invention. Under preparatory conditions, the additives such as a stabilizer and isotonizing agent may be added after the fat emulsions have been formed.

The fat emulsions may be administered parenterally such as by injection, most preferably intravenously. For instance, the prostaglandin $I_2$'s are administered intravenously by continuous infusion once a day in dose levels of 0.01–0.1 µg/kg, or 0.01–0.1 ng/kg/min. The fat emulsions in the present invention possess very potent effects, are long-acting by sustained release and selective for lesions; therefore, administration of small doses enables effective treatment.

Since intravenous administration is possible, rapid onset of action can be anticipated, drug efficacy is consistent, and since doses are small, there is less manifestation of side effects.

Furthermore, the particles are extremely minute, and the average size of them is less than 1.0 µ. The safety (stability) during storage is very good.

Best Manner to Implement the Invention

Using the following Examples, the best methodologies to embody the present invention are described below:

EXAMPLE 1

Preparation of a fat emulsion containing isocarbacyclin (compound I)

To 10 g of a refined soybean oil were added 1.2 g of egg yolk lecithin and 1000 µg of isocarbacyclin. The mixture was heated at 60–80° C. to a solution. To this solution were added 50 ml of distilled water and then 2.5 g of glycerol. Distilled water for injection was added to make the solution to 100 ml. The solution was roughly emulsified in a homomixer.

Using a Manton-Gaulin homogenizer, the crude emulsion was then further emulsified by passing 10 times through the instrument under a first-stage pressure of 120 kg/cm² and a total pressure of 500 kg/cm². There was obtained a homogenized, finely dispersed, 10 % soybean oil-containing fat emulsion which contained isocarbacyclin (compound I) in a final concentration of 10 µg/ml.

EXAMPLE 2

Preparation of the fat emulsions, each of which contained
16,17,18,19,20-pentanor-15-pentylisocarbacyclin (compound II), 7-fluoro-16,17,18,19,
20-pentanor-15-cyclopentylprostacyclin methyl ester (compound III), and isocarbacyclin methyl ester (compound IV), respectively Using compounds II, III, and IV, the 10% soybean oil-containing fat emulsions were prepared in the same manner as in Example 1, each of which contained the above-mentioned compound respectively, in a final concentration of 5 µg/ml, 5 µg/ml, and 10 µg/ml, respectively.

EXAMPLES 5–16

Evaluation of drug activities using human platelets

The time course of the formation of cyclic AMP by the fat emulsion in the invention was determined using human platelets so as to compare with the time course of the compound which was not emulsified in fat. Human blood 50 ml was collected using 1 part of 3.8 % sodium citrate for 9 parts of blood. The blood sample was centrifuged at 1300 rpm for 10 minutes. The upper layer was taken out as PRP (platelet-rich plasma) and centrifuged at 3000 rpm for 20 minutes. The precipitate thus obtained (platelets) was suspended in 2 ml of Tris buffered solution-saline-glucose-EDTA (TSG-EDTA) (pH 7.4).

The fat emulsion, which had previously been transferred in a plastic tube containing 350 µl of TSG-EDIA and 50 µl of platelet suspension and incubated at 37° C., was supplemented with 50 µl of 5mM isobutylmethylxanthin dissolved in saline, and 2 minutes later, reactions were stopped with 0.5 ml of 10% trichloroacetic acid (TCA). The cells were destroyed by thawing the lyophilized specimen in order to release intracellular cyclic AMP. After removal of TCA with watersaturated ether, the content of C-AMP was determined by radio immunoassay technique.

The results are summarized in Table 1. As is clear from these results, it was demonstrated that the production capability of C-AMP by the fat emulsion was satisfactorily maintained over time.

TABLE 1

Production capability and maintenance of cyclic AMP by fat emulsions

| Examples | Compounds | Time (min.) | C-AMP production (pico mol) | Relative value (%) |
|---|---|---|---|---|
| Example 5 | Fat emulsion (I) | 0 | 80 | 100 |
| Example 6 | " | 30 | 100 | 125 |
| Example 7 | " | 60 | 100 | 125 |
| Comparison 1 | Compound (I) | 0 | 320 | 100 |
| Comparison 2 | " | 30 | 200 | 63 |
| Comparison 3 | " | 60 | 100 | 31 |
| Example 8 | Fat emulsion (II) | 10 | 130 | 100 |
| Example 9 | " | 30 | 190 | 146 |
| Example 10 | " | 60 | 100 | 76 |
| Comparison 4 | Compound (II) | 10 | 430 | 100 |
| Comparison 5 | " | 30 | 320 | 74 |
| Comparison 6 | " | 60 | 120 | 27 |
| Example 11 | Fat emulsion (III) | 30 | 55 | 100 |

TABLE 1-continued

Production capability and maintenance of cyclic AMP by fat emulsions

| Examples | Compounds | Time (min.) | C-AMP production (pico mol) | Relative value (%) |
|---|---|---|---|---|
| Example 12 | " | 60 | 30 | 55 |
| Example 13 | " | 120 | 30 | 55 |
| Comparison 7 | Compound (III) | 30 | 100 | 100 |
| Comparison 8 | " | 60 | 90 | 90 |
| Comparison 9 | " | 120 | 40 | 40 |
| Example 14 | Fat emulsion (IV) | 30 | 40 | 100 |
| Example 15 | " | 30 | 45 | 111 |
| Example 16 | " | 120 | 28 | 70 |

EXAMPLE 17

Determination of platelet agglutination inhibitory action

Fifty (50) μl of the fat emulsion obtained in Examples 1 and 2 was transferred into 950 μl of saline or 2 % bovine serum albumin (BSA) and incubated at 37° C. for 1, 3, and 10 minutes. Next, the ADP platelet agglutination inhibitory action by PRP was determined using the filtrate which had been passed through a 0.025 μm filter. A known quantity of the dilution before filtration was added to PRP and incubated at 37° C. for 1 minute. Thereafter, ADP agglutination was induced to construct a dose-response curve. The platelet agglutination inhibitory action was calculated from this curve. The results are presented in Table 2.

TABLE 2

Platelet agglutination inhibitory action

| Conditions | | Platelet agglutination inhibitory action (%) | | | |
|---|---|---|---|---|---|
| Dilutions | Incubation time (min.) | Fat elulsion (IV) | Compound (IV) | Fat emulsion (I) | Compound (I) |
| 2% BSA | 1 | 13.7 | 65.4 | 87.5 | 100.1 |
| | 3 | 23.1 | NT | 83.5 | NT |
| | 10 | 27.1 | 56.2 | 90.6 | 107.7 |
| Saline | 10 | — | — | 14.1 | 41.1 |

As indicated in Table 2, in the fat emulsions in the present invention, the active ingredient of the prostaglandin I$_2$'s is gradually released, and thus these dosage forms provide a sustained-release delivery.

Potential applications in industry

The fat emulsions containing the prostaglandin I$_2$'s in the present invention possess potent effects, provide a sustained-release delivery, and are selective for lesions. Therefore, they can provide effective therapy in small doses and are extremely useful in the treatment of various kinds of cardio-vascular diseases such as thrombotic diseases.

What is claimed is:

1. A pharmaceutical prostaglandin emulsion comprising:

a mixture of vegetable oil, phospholipid, water, and a pharmaceutically effective amount of at least one compound of formula (Ia)

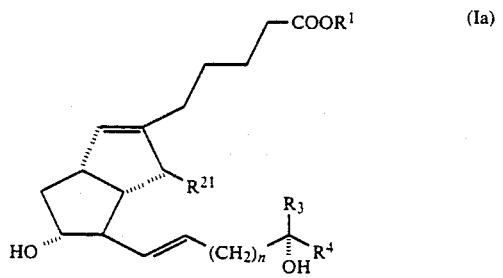

wherein $R^1$ is selected from the group consisting of a hydrogen atom and an unsubstituted alkyl group having 1 to 10 carbon atoms;

$R^{21}$ is a hydrogen atom;

$R^3$ is a hydrogen atom;

$R^4$ is an unsubstituted alkyl group having 1-10 carbon atoms; and n represents 0.

2. The pharmaceutical prostaglandin emulsion according to claim 1, wherein $R^1$ is a methyl group and $R^4$ is a pentyl group.

3. The pharmaceutical prostaglandin emulsion according to claim 1, wherein said mixture comprises 5-50% (w/v) vegetable oil, 1-50 parts of phospholipid per 100 parts vegetable oil, from 1.0 mg/ml to 0.2 μg/ml of said compound of formula (Ia) and the balance water.

* * * * *